United States Patent [19]

Buchanan, Jr.

[11] Patent Number: 5,041,564

[45] Date of Patent: Aug. 20, 1991

[54] VAPOR PHASE PROCESS FOR PRODUCTION OF GAMMA-BUTYROLACTONE

[75] Inventor: Donald W. Buchanan, Jr., Wayne, N.J.

[73] Assignee: GAF Chemicals Corporation, Wayne, N.J.

[21] Appl. No.: 509,431

[22] Filed: Apr. 16, 1990

[51] Int. Cl.$^5$ .............................................. C07D 307.32
[52] U.S. Cl. .................................... 549/325; 549/326
[58] Field of Search .............................. 549/325, 326

[56] References Cited

U.S. PATENT DOCUMENTS

| | | | |
|---|---|---|---|
| 3,065,243 | 11/1962 | Dunlop et al. | 549/325 |
| 3,580,930 | 5/1971 | Miya et al. | 549/325 |
| 3,853,922 | 12/1974 | Yamaguchi et al. | 549/325 |
| 3,948,803 | 4/1976 | Carney | 549/3 |
| 3,980,670 | 9/1976 | Kammer et al. | 549/326 |
| 4,001,282 | 1/1977 | Miller | 549/325 |
| 4,006,165 | 2/1977 | Michalczyk et al. | 549/325 |
| 4,032,458 | 6/1977 | Cooley et al. | 568/864 |
| 4,048,196 | 9/1977 | Broecker et al. | 549/325 |
| 4,083,809 | 4/1978 | De Thomas et al. | 502/245 |
| 4,105,674 | 8/1978 | De Thomas et al. | 549/326 |
| 4,256,675 | 3/1981 | Vanderspurt et al. | 558/315 |
| 4,810,807 | 3/1989 | Budge et al. | 549/508 |

FOREIGN PATENT DOCUMENTS

| | | | |
|---|---|---|---|
| 322140 | 6/1989 | European Pat. Off. | 549/325 |
| 1168220 | 4/1967 | United Kingdom | 549/325 |
| 1293151 | 10/1969 | United Kingdom | 549/429 |

Primary Examiner—Richard L. Raymond
Assistant Examiner—Mark W. Russell
Attorney, Agent, or Firm—Walter Katz; Marilyn J. Maue; Joshua J. Ward

[57] ABSTRACT

What is provided herein is a vapor phase process for the production of butyrolactone in which the vapor mixture of the feed compound and hydrogen is provided at high flow rates from finely divided droplets of the feed compound which are vaporized rapidly with hot hydrogen gas.

15 Claims, 1 Drawing Sheet

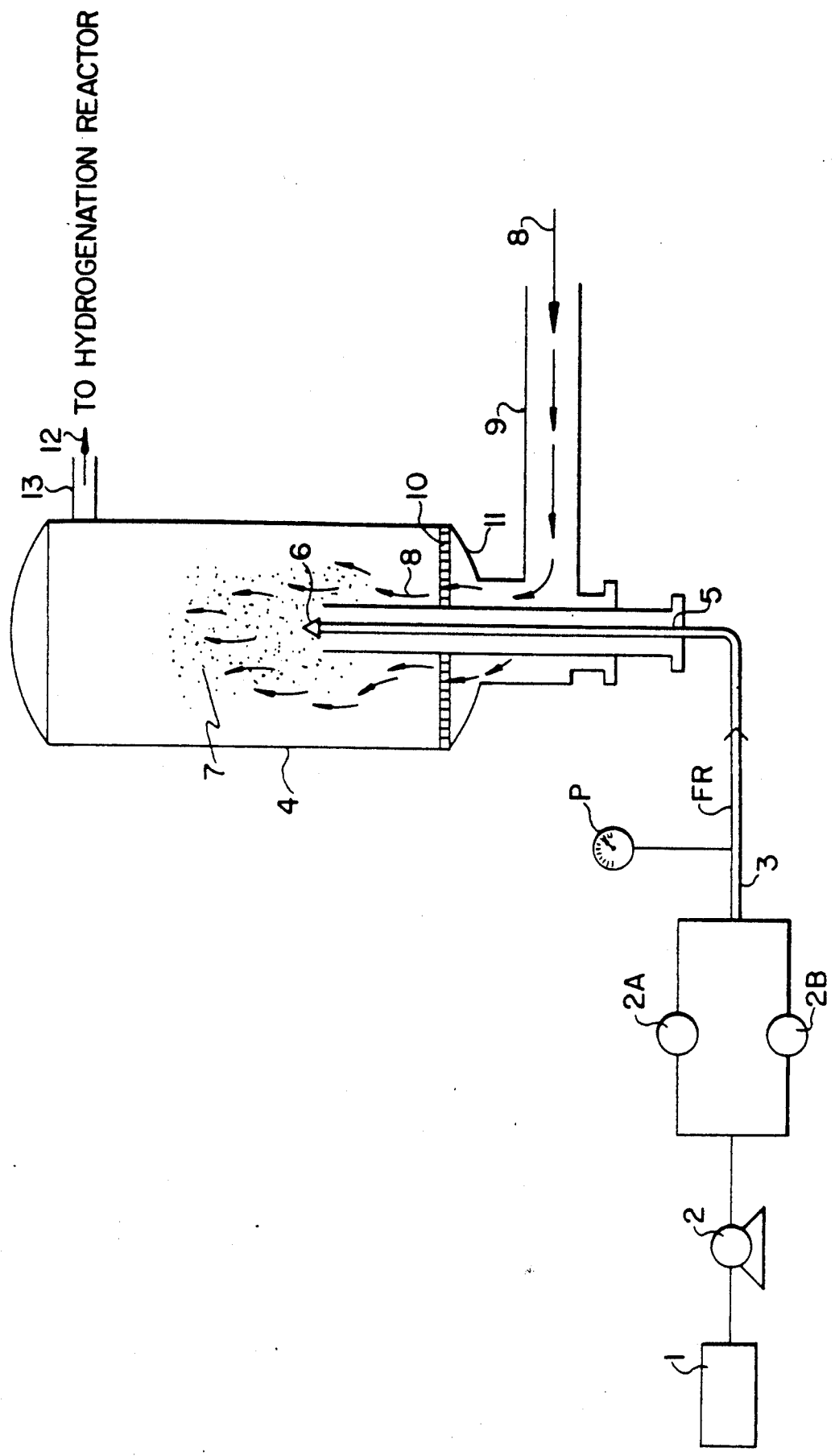

VAPOR PHASE PROCESS FOR PRODUCTION OF GAMMA-BUTYROLACTONE

BACKGROUND OF THE INVENTION

1. Field of the Invention

This invention relates to a vapor phase process for the production of gamma-butyrolactone, and, more particularly, to a method and apparatus for forming a vapor mixture of a feed compound and hydrogen in such process.

2. Description of the Prior Art

Gamma-butyrolactone is a stable, well-known compound that is a liquid at −44° C. to 204° C. It is used as an intermediate in the manufacture of 2-pyrrolidone, alpha-tetralone and glutaric acid; in the solvent welding of plastic films; as a swelling agent for cellulose acetate films; and as a non-corrosive solvent for polymers in general, acetylene and water-immiscible alcohols.

In general, the catalytic hydrogenation of maleic anhydride and/or other related compounds to produce gamma-butyrolactone (hereinafter referred to as "butyrolactone") is an old and well established art for which a great many processes have been used, the most important of which historically have been effected in the liquid phase.

An alternative to the commercially-used, liquid phase catalytic hydrogenation of maleic anhydride, succinic anhydride, etc. feedstocks is vapor phase hydrogenation, at low pressures, in the presence of a generally different class or type of catalyst. Exemplary of patents covering vapor phase catalytic hydrogenation of conventional feedstocks to butyrolactone include, for example, U.S. Pat. No. 3,065,243, wherein the conversion to butyrolactone is effected at low pressures in the presence of a copper chromite catalyst.

De Thomas, in U.S. Pat. No. 4,105,674, also described a vapor phase process in which the feed reactant mixture was formed by passing hydrogen through maleic anhydride in a vaporizer maintained at a temperature of 130°–190° C. However, in this method, the rate of vaporization of liquid maleic anhydride did not provide a suitable flow rate of reactant for commercial production of butyrolactone. Furthermore, maleic anhydride reacts with recycle components at these temperatures.

Attig, in EPA 332,140, published Jun. 28, 1989, described a vapor phase, catalytic hydrogenation of maleic anhydride to tetrahydofuran and butyrolactone. In this process, the vapor mixture of maleic anhydride and hydrogen was formed by pumping molten maleic anhydride into a stream of hydrogen in a vaporizer at 155° C.
However, the rate of vaporization of maleic anhydride was limited by the slow transfer of heat from hydrogen gas to the mass of molten maleic anhydride.

Other pertinent references in this field include U.S. Pat. Nos. 3,580,930; 3,894,054; 4,032,458; 3,853,922; 3,948,805; 4,001,282; 4,006,165; 4,032,458; 4,048,196; 4,083,809; 4,105,674; 4,810,807; and U.K. patent Nos. 1,168,220 and 1,293,151.

Commercial practice in respect of the production of butyrolactone from a vapor mixture of maleic anhydride and hydrogen by catalytic hydrogenation has not been entirely successful, not only because of the short lifetime afforded by conventional hydrogenation catalysts, but also because of the low rate of vaporization of molten maleic anhydride into a hydrogen stream, particularly a hot, reactive recycle hydrogen stream.

It is also well known that heating to elevated temperatures, e.g. above 135° C. can cause rapid decomposition/charring of maleic anhydride.

Accordingly, it is an object of this invention to provide an improved vapor process for the production of butyrolactone from a vapor mixture of a feed compound such as maleic anhydride and hydrogen.

Another object of the present invention is to provide a process for forming a high flow rate of feed compound in recycle hydrogen gas.

Still another object herein is to provide a continuous vapor process including a vaporizer apparatus in which a liquid feed compound is converted into finely divided droplets which can be vaporized rapidly in hot, recycle hydrogen gas.

Another object is to vaporize maleic anhydride in an extremely short time at elevated temperatures and before decomposition can take place.

Yet another object is to provide a vaporization process in which there is a relatively low pressure drop between the recycle hydrogen gas entering and leaving the vaporizer as compared to other vaporization processes known in the art.

These and other objects and features of the invention will be made apparent from the following more particular description of the invention.

SUMMARY OF THE INVENTION

What is provided herein is a vapor phase process and apparatus for the production of butyrolactone in which the vapor mixture of the feed compound and recycle hydrogen is provided at high flow rates formed from finely divided droplets of the feed compound which can be vaporized rapidly with hot, recycle hydrogen gas.

BRIEF DESCRIPTION OF THE DRAWING

The FIGURE is a schematic illustration of a vapor phase process for the production of butyrolactone including the vaporizer apparatus of the invention for forming a vapor mixture of feed compound and recycle hydrogen.

DETAILED DESCRIPTION OF THE INVENTION

Referring now to the drawings, the FIGURE is a schematic illustration of the vapor phase process of the invention for the production of butyrolactone by catalytic hydrogenation of a vapor mixture of a feed compound in hydrogen. Suitable feed compounds include maleic anhydride, maleic acid, succinic anhydride and succinic acid, or esters therefrom, such as diethyl maleate or diethyl succinate. What is shown therein is a source of a feed compound 1 such as molten maleic anhydride at about 80° C. The maleic anhydride is pumped by a pulse dampened, displacement pump 2 through filters 2A and 2B through conduit 3 at a suitable pressure P and flow rate FR into vaporizer vessel 4 through inlet tube 5. The inlet tube 5 terminates in a spray nozzle 6 which can convert the mass of molten liquid into fine droplets 7 within the interior of the vessel.

A hot, recycle hydrogen gas stream 8 then is introduced into the vessel in the direction indicated by the arrows through inlet pipe 9 at an inlet temperature of about 160° to 325° C., preferably about 200° to 300° C. The recycle hydrogen gas contacts droplets 7 to vaporize them substantially immediately, and, preferably, before the droplets reach the relatively cold walls of the vessel where they might coalesce into a liquid stream or decompose and char to a non-volatile solid. An optional distributor plate 10 is provided at the base 11 of vessel 4 which is positioned circumferential of inlet pipe 9 to ensure that the recycle hydrogen flow 8 is directed axially against the droplets. Generally the hot hydrogen gas is provided by recycling hydrogen from the hydrogenation reactor (not shown). This recycle hydrogen gas is introduced into the vaporizer in an amount in substantial excess of the stoichiometric amount of hydrogen required for conversion of maleic anhydride to butyrolactone.

The feed maleic anhydride liquid may be heated, if desired by the hot recycle hydrogen gas enroute to the nozzle up to about 170°–190° C. The heated maleic anhydride droplets then are vaporized in the vaporizer within about $\frac{1}{4}$ to 1 second. Therefore, substantially no decomposition or charring reactions occur during vaporization of the droplets. In fact, the nozzle orifice remains open and operative even after 2000 or more hours of continuous production of such vapor mixtures.

The pressure of the molten maleic anhydride which enters the nozzle suitably is set at about 250 to 1000 psig. The maleic anhydride droplets are formed into the recycle hydrogen gas, which is usually at a pressure of about 100–500 psig. Accordingly, a pressure drop of about 100 to 900 psig is established between the inlet line and interior of the vaporizer vessel. This pressure drop furnishes the energy required to form suitable fine droplets, which usually have a Sauter mean diameter of about 30–100 microns.

The vapor stream 12 of maleic anhydride in excess hydrogen exits from the vaporizer through outlet pipe 13 at a temperature of about 120° to 285° C., preferably about 150° to 280° C. These exit stream temperatures usually provide suitable inlet temperatures for the hydrogenation reaction; however, the vapor stream may be further heated as required for the hydrogenation reaction.

While the nozzle is shown as directed upwardly in vaporizer vessel 4, it will be understood that a downward or angular flow of droplets, or a combination thereof, also may be used.

As described, hydrogen is supplied to the vaporizer in a stoichiometric excess of hydrogen to the feed compound. The vapor stream preferably is formed in a molar ratio of about 200:1 to 400:1 of hydrogen to feed compound.

The invention will now be illustrated by reference to the following working example.

EXAMPLE I

Commercial grade molten maleic anhydride was charged into a tank wagon which was steam traced at 80°–100° C. A centrifugal pump was provided to circulate the molten maleic anhydride (MA) in the tank wagon and to direct the flow of molten liquid into a feed tank for charging. The pressure of molten MA required to spray the feed compound through a spray nozzle was developed by a plunger-type, positive displacement metering pump. The equipment delivered molten maleic anhydride at a flow rate of about 10 pounds of MA per hour to the spray nozzle.

The liquid pressure was about 425 psig. The nozzle employed in the vaporizer was a Delavan WDA 0.75, Lexington, TN, having an upwardly directed, 45 degree hollow cone spray and an orifice size of 0.0092 inches. The fine spray droplets developed by this nozzle were contacted with recycle hydrogen at 160° C. at a pressure of 150 psig. The recycle gas had a composition which included 98.9 mole % $H_2$. The recycle hydrogen stream was directed axially of the vaporizer walls to vaporize the droplets within a period of about $\frac{1}{4}$ second.

The exiting vapor stream was cooled to 140° C. due to the adiabatic vaporization of MA liquid; it contained about 0.42 mole % of MA. This vapor stream then was passed into a catalytic reactor for conversion of MA into butyrolactone.

The vaporizer was operated continuously for 1124 hours without failure. An effective catalytic hydrogenation reaction was obtained during this period.

EXAMPLE 2

The procedure of Example 1 was followed using a recycle hydrogen temperature of 265° C., and a flow rate of about 15 pounds of MA per hour, fed into a $\frac{1}{4}$ LN.60 spray nozzle sold by Spraying Systems, Inc., Wheaton, IL, having an orifice size of 0.016 inches. The exit gas stream was cooled to 240° C. Similar results were obtained with respect to effective production of the desired vapor maleic anhydride-$H_2$ stream, and subsequent hydrogenation.

While the invention has been described with particular reference to certain preferred embodiments thereof, it will be understood that changes and modifications may be made which are within the skill of the art. Accordingly, it is intended to be bound only by the appended claims.

What is claimed is:

1. In a vapor phase process for the production of gamma-butyrolactone by catalytic hydrogenation of a vapor stream of a feed compound selected from maleic anhydride, maleic acid, succinic anhydride, succinic acid, and esters thereof, and mixtures thereof, in hydrogen, the steps which comprises:
   (a) in a vaporizer vessel, forming finely divided liquid droplets of said feed compound, and
   (b) introducing hot, recycle hydrogen gas into said vessel to rapidly vaporize substantially all of aid droplets by contact therewith to form a vapor mixture of said feed compound in hydrogen.

2. A vapor phase process according to claim 1 wherein said feed compound is maleic anhydride.

3. A vapor phase process according to claim 1 wherein the inlet temperature of the hot recycle hydrogen gas is maintained at a temperature of about 140° to 325° C.

4. A vapor phase process according to claim 3 wherein said inlet temperature is about 150° to 300° C.

5. A vapor phase process according to claim 2 wherein said droplets are formed from molten maleic anhydride introduced into the vaporizer at a temperature of about 80° C.

6. A vapor phase process according to claim 1 wherein said droplets are formed by pumping a molten feed compound through a spray nozzle.

7. A vapor phase process according to claim 1 wherein said droplets are formed upwardly, downwardly or angularly, or a combination thereof.

8. A vapor phase process according to claim 1 wherein said hot, recycle hydrogen gas is applied axially or angularly of said droplet stream.

9. A vapor phase process according to claim 1 wherein the vapor stream of feed compound in hydrogen is formed in a stoichiometric excess of hydrogen to the feed compound in the range of about 200:1 to 400:1.

10. A vapor phase process according to claim 9 wherein said ratio is about 230:1 to 350:1

11. A vapor phase process according to claim 1 wherein the droplets have a Sauter mean diameter of about 5 to 100 microns.

12. A vapor phase process according to claim 1 wherein the vapor mixture is exited from the vaporizer vessel at a temperature of about 140° to 300° C.

13. A vapor phase process according to claim 12 wherein said exit temperature is about 230° to 230° C.

14. A vapor phase process according to claim 6 wherein the pressure of the feed compound entering the nozzle is about 250 to 1000 psig and the pressure drop upon forming the droplets in the vaporizer vessel is about 100 to 850 psig.

15. A vapor phase process according to claim 1 wherein the vapor feed stream is passed over a hydrogenation catalyst to form gamma-butyrolactone.

* * * * *